(12) United States Patent
Chiu

(10) Patent No.: US 10,946,115 B2
(45) Date of Patent: Mar. 16, 2021

(54) HUMIDIFIER WITH REGULAR ADDITION OF FIXED QUANTITY OF ESSENTIAL OIL

(71) Applicant: Pao-Tien Chiu, New Taipei (TW)

(72) Inventor: Pao-Tien Chiu, New Taipei (TW)

( * ) Notice: Subject to any disclaimer, the term of this patent is extended or adjusted under 35 U.S.C. 154(b) by 0 days.

(21) Appl. No.: 16/739,672

(22) Filed: Jan. 10, 2020

(65) Prior Publication Data

US 2020/0147257 A1 May 14, 2020

Related U.S. Application Data

(63) Continuation-in-part of application No. 15/893,236, filed on Feb. 9, 2018, now Pat. No. 10,571,138.

(51) Int. Cl.
*A61L 9/14* (2006.01)
*F24F 6/02* (2006.01)

(52) U.S. Cl.
CPC ........ *A61L 9/14* (2013.01); *F24F 6/02* (2013.01); *A61L 2209/133* (2013.01); *A61L 2209/134* (2013.01)

(58) Field of Classification Search
CPC .............. A61L 9/14; A61L 2209/133; A61L 2209/134; F24F 6/02
USPC ............ 261/18.2, 30, 34.1, 37, 72.1, 81
See application file for complete search history.

(56) References Cited

U.S. PATENT DOCUMENTS

| | | | |
|---|---|---|---|
| 2,736,538 A | 2/1956 | Barlow | |
| 3,942,915 A * | 3/1976 | Thomas | F04B 43/1253 417/360 |
| 5,249,937 A * | 10/1993 | Aubert | F04B 43/1292 417/475 |
| 5,549,247 A | 8/1996 | Rossman et al. | |
| 6,029,711 A * | 2/2000 | Koch | F04B 43/0072 138/118 |
| 6,786,474 B2 | 9/2004 | Watkins et al. | |
| 7,878,418 B2 | 2/2011 | Sevy | |
| 8,807,538 B2 | 8/2014 | Sharma | |
| 10,571,138 B2 * | 2/2020 | Chiu | F24F 6/02 |
| 2002/0153622 A1 | 10/2002 | Hugon | |

FOREIGN PATENT DOCUMENTS

CN 207831563 U 9/2018
CN 109899926 A 6/2019

* cited by examiner

*Primary Examiner* — Charles S Bushey
(74) *Attorney, Agent, or Firm* — Muncy, Geissler, Olds & Lowe, P.C.

(57) ABSTRACT

A humidifier with regular addition of fixed quantity of essential oil has a main body, and a water storage bucket assembling with the main body. The main body has an opening located on one side, an inner casing corresponding to the opening, and a peristaltic pump provided on a side of the inner casing not facing the opening. The inner casing defines an essential oil bottle accommodation space communicating with the opening, and the essential oil bottle accommodation space is provided for disposing an essential oil bottle storing an essential oil. The peristaltic pump is controlled by the main body, thereby fixed quantity of essential oil is supplied regularly and quantitatively by the humidifier without dismounting the water storage bucket. Thus, fragrance is kept in atomizing air continuously to solve the problem of the conventional humidifier that fragrance merely exists when the essential oil is added initially.

9 Claims, 17 Drawing Sheets

HUMIDIFIER WITH REGULAR ADDITION OF FIXED QUANTITY OF ESSENTIAL OIL

CROSS-REFERENCE TO RELATED APPLICATION

This application is a continuation-in-part, and claims priority, from U.S. patent application Ser. No. 15/893,236 filed on Feb. 9, 2018, now U.S. Pat. No. 10,571,138 entitled "HUMIDIFIER WITH REGULAR ADDITION OF FIXED QUANTITY OF ESSENTIAL OIL HUMIDIFIER WITH REGULAR ADDITION OF FIXED QUANTITY OF ESSENTIAL OIL", the entire contents of which are hereby incorporated by reference.

FIELD OF THE INVENTION

The present invention is related to a humidifier, particularly to a humidifier with regular addition of fixed quantity of essential oil capable of being located in public areas.

BACKGROUND OF THE INVENTION

When the weather is cold, heating equipment or heaters are used in many public places or houses to increase room temperature. During the use of heaters, air is dried to cause discomfort. For this reason, humidifiers are used by many users while the heaters are turned on, so as to eliminate the problem of dry air via the humidifiers.

Recently, the addition of essential oil is desired by a part of users during the use of humidifiers, so as to improve psychic state via fragrance generated by the essential oil. If the addition of essential oil in the humidifier is desired recently, however, it is only possible to drop the essential oil into the atomization reaction zone without the water box being mounted to the humidifier such that essential oil is volatilized to generate fragrance while atomization reaction is performed in the humidifier. Nevertheless, the specific gravity of essential oil is lower than the specific gravity of water, such that the essential oil will float on water. In this way, the essential oil is atomized and volatilized rapidly, and thus the time period when mist contains fragrance may not meet expectations. Therefore, it is necessary for the user to disassemble and assemble the humidifier several times to keep mist containing fragrance continuously, which is truly inconvenient.

A conventional humidifier structure is revealed in China Patent No. CN 2078315630, wherein the conventional humidifier is provided with an essential oil supplier to add fragrance to the atomized air. However, according to the description of CN 2078315630, the conventional humidifier must be provided with a peristaltic pump for each essential oil bottle when a user desires to use different essential oils for the humidifier. That is, when the user intends to change to a different essential oil, the user must replace the entire set of essential oil supplier, which will result in an increase in the cost of use.

On the other hand, China Patent No. CN 109899926A also provides the technical means by which humidifiers can be added with fragrance during implementation, however, according to the description of CN 109899926A, when the user desires to add different fragrant essential oils to the humidifier, it is impossible for the user to replace the flexible tube and different essential oils simultaneously since the flexible tube for extracting essential oils is fixed in the humidifier. As a result, essential oils with different fragrances are mixed in the flexible tube, so that the scent of fragrance used in the humidifier is changed.

SUMMARY OF THE INVENTION

A main object of the present invention is to solve the problem that the peristaltic pump needs to be simultaneously replaced when the conventional humidifier is used with different essential oil bottles.

A secondary objective of the present invention is to solve the problem that the flexible tube in the conventional humidifier cannot be replaced together when replacing different essential oils, which causes different essential oils to be mixed in the flexible tube.

In order to achieve the above objects, the present invention provides a humidifier with regular addition of fixed quantity of essential oil. The humidifier includes a main body, and a water storage bucket assembling with the main body. The main body comprises a temporary liquid storage basin, an atomizing space defined by the temporary liquid storage basin, an atomizing plate disposed within the temporary liquid storage basin, a projecting stud disposed within the temporary liquid storage basin, a fan generating air stream within the atomizing space after being started, and a startup management module connected to the fan and the atomizing plate. A high water level line is defined on the temporary liquid storage basin. The water storage bucket comprises a bucket body, a water supply switch provided on the bucket body and pushed by the projecting stud to permit water stored in the water storage bucket to flow into the temporary liquid storage basin, and an air guiding passage defined and formed by the bucket body while communicated to the atomizing space without being used for water storage. Further, the main body comprises at least one opening located on one side, an inner casing disposed inside the main body and corresponding to the opening, and a peristaltic pump provided on a side of the inner casing not facing the opening. The inner casing defines an essential oil bottle accommodation space communicating with the opening, the inner casing is disposed with a through hole and an tube, wherein the through hole is provided for a transmission shaft of the peristaltic pump to pass through, and one end of the tube faces the temporary liquid storage basin. The humidifier comprises a peristaltic pump head provided in the essential oil bottle accommodation space and driven by the peristaltic pump, in the peristaltic pump head is provided with a plurality of rollers driven by the transmission shaft, and a liquid delivering hose disposed between the plurality of rollers, one end of the liquid delivering hose reaches into an essential oil bottle, and another end is connected to the tube.

In one embodiment, the main body comprises a lid disposed corresponding to the opening to seal the essential oil bottle accommodation space.

In one embodiment, the inner casing comprises two limit plates spaced apart from each other, a pump head installation zone is defined by the two limit plates, and the through hole and one end of the essential oil delivering tube are located in the pump head installation zone.

In one embodiment, the inner casing comprises a connecting plate connected to the two limit plates and the pump head installation zone is defined by the connecting plate together with the two limit plates.

In one embodiment, the peristaltic pump head is provided with a connecting arm on both sides respectively, and each of the two limit plates comprises a positioning structure assembled with the connecting arm.

In one embodiment, the connecting arm is provided with a hook at one end assembled with the positioning structure.

In one embodiment, each positioning structure is a through hole providing for one of the hooks to dispose.

In one embodiment, the main body comprises a protective cover disposed on a side of the inner casing that does not face the opening and covering the peristaltic pump.

In one embodiment, the main body includes a plurality of control switches connected to the startup management module and exposed outside the main body.

Through the foregoing disclosure of the present invention, the present invention has the following characteristics compared with the conventional humidifiers: the present invention forms the essential oil bottle accommodation space through the inner casing, so that the peristaltic pump head and the essential oil bottle can be placed in the main body, thereby reducing the possibility that the peristaltic pump head and the essential oil bottle subject to external impact. In addition, the peristaltic pump of the invention is not provided on the peristaltic pump head, so that when a user desires to replace the different essential oil bottles located within the humidifier, the user does not have to replace together with the peristaltic pump, thereby greatly reducing the cost for consumers. Furthermore, because the liquid delivering hose is provided in the peristaltic pump head, the user can dismount the liquid delivering hose when replacing the different peristaltic pump head and the essential oil bottle. Thus, the scent of fragrance used in the humidifier is unchanged since the essential oil with different fragrances is prevented from mixing in the liquid delivering hose.

DETAILED DESCRIPTION OF THE PREFERRED EMBODIMENTS

Figure 1:
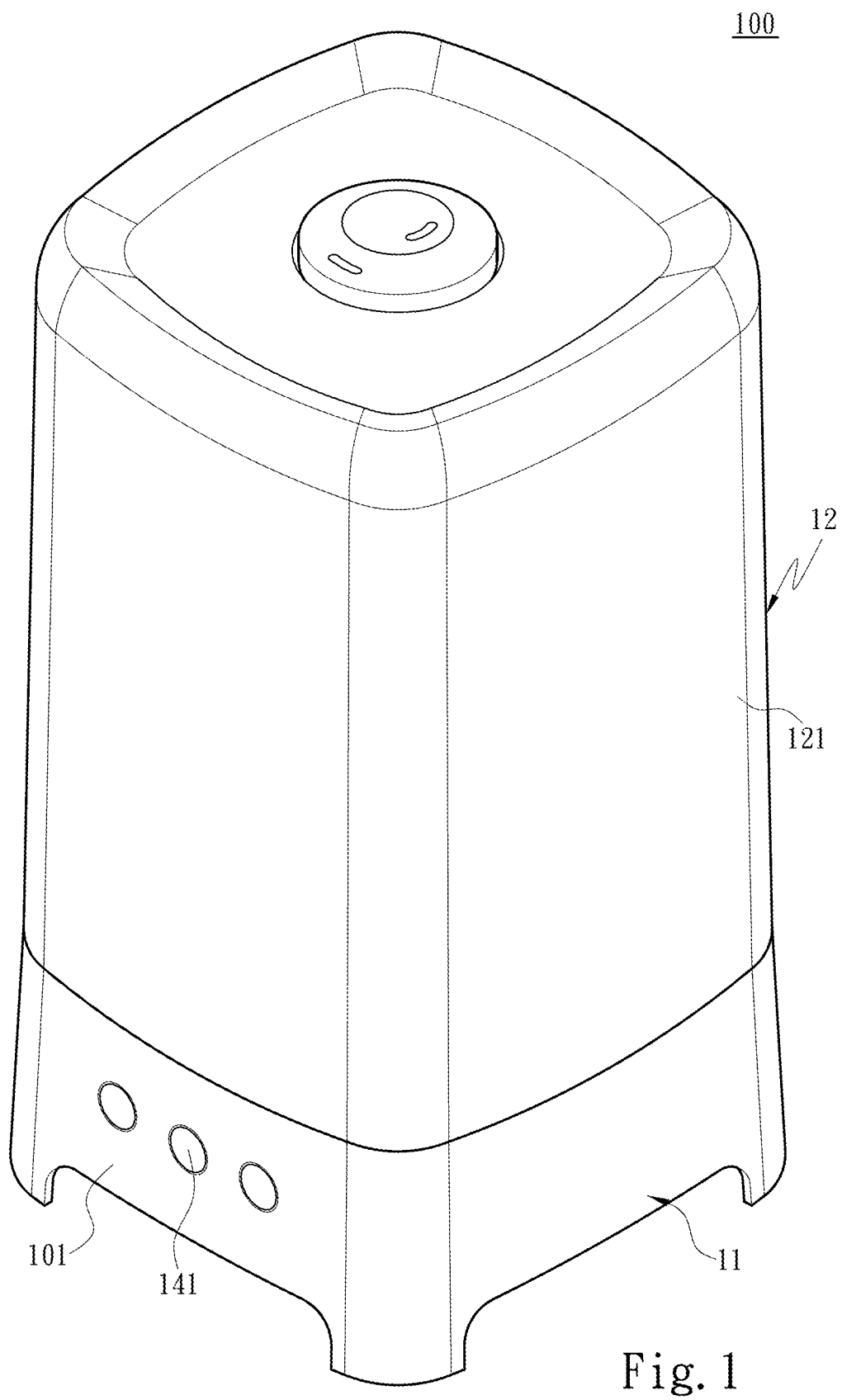
FIG. 1 is a structural view of one embodiment of the present invention.
Figure 2:
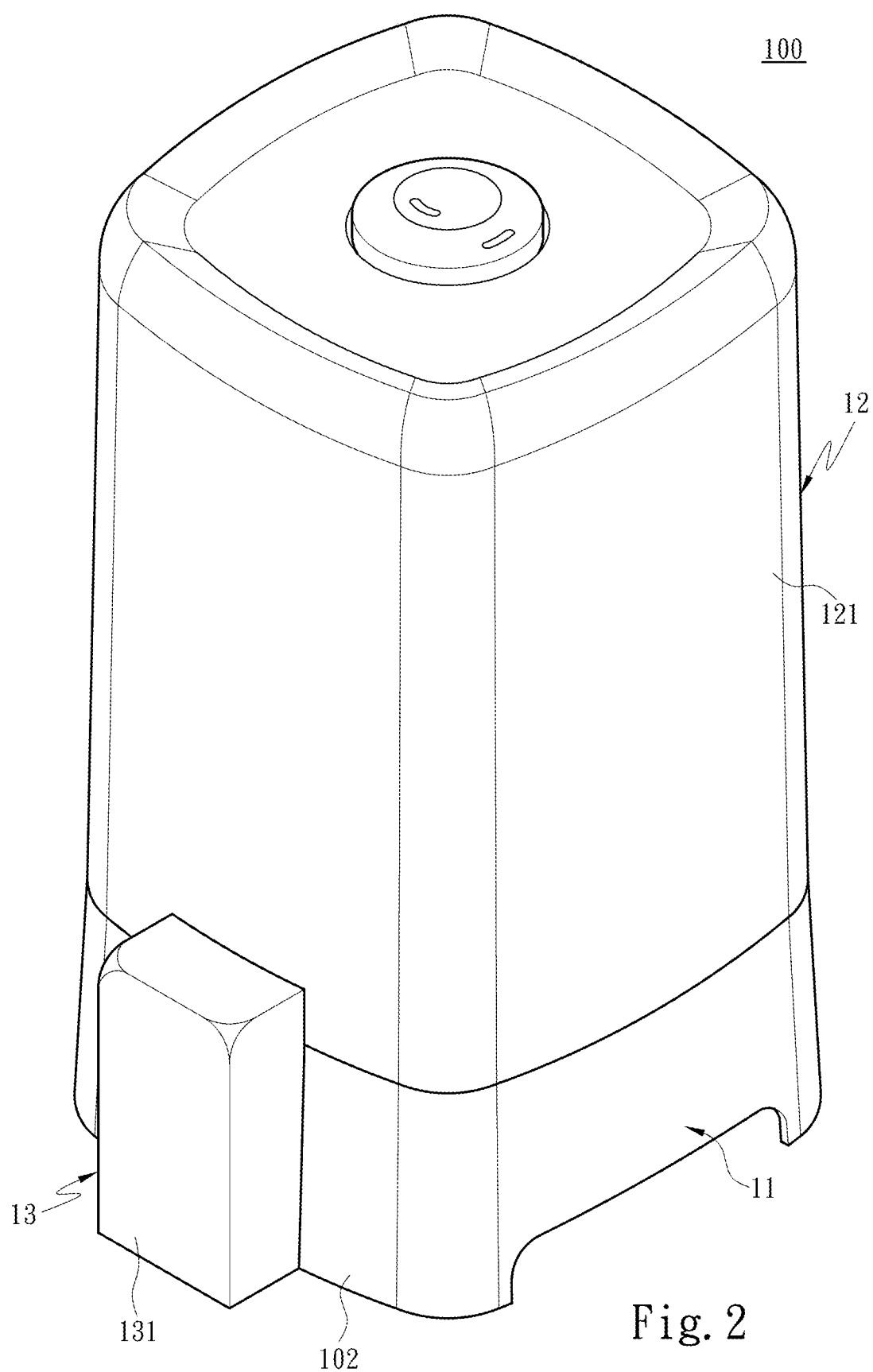
FIG. 2 is a structural view in another direction of one embodiment of the present invention.
Figure 3:
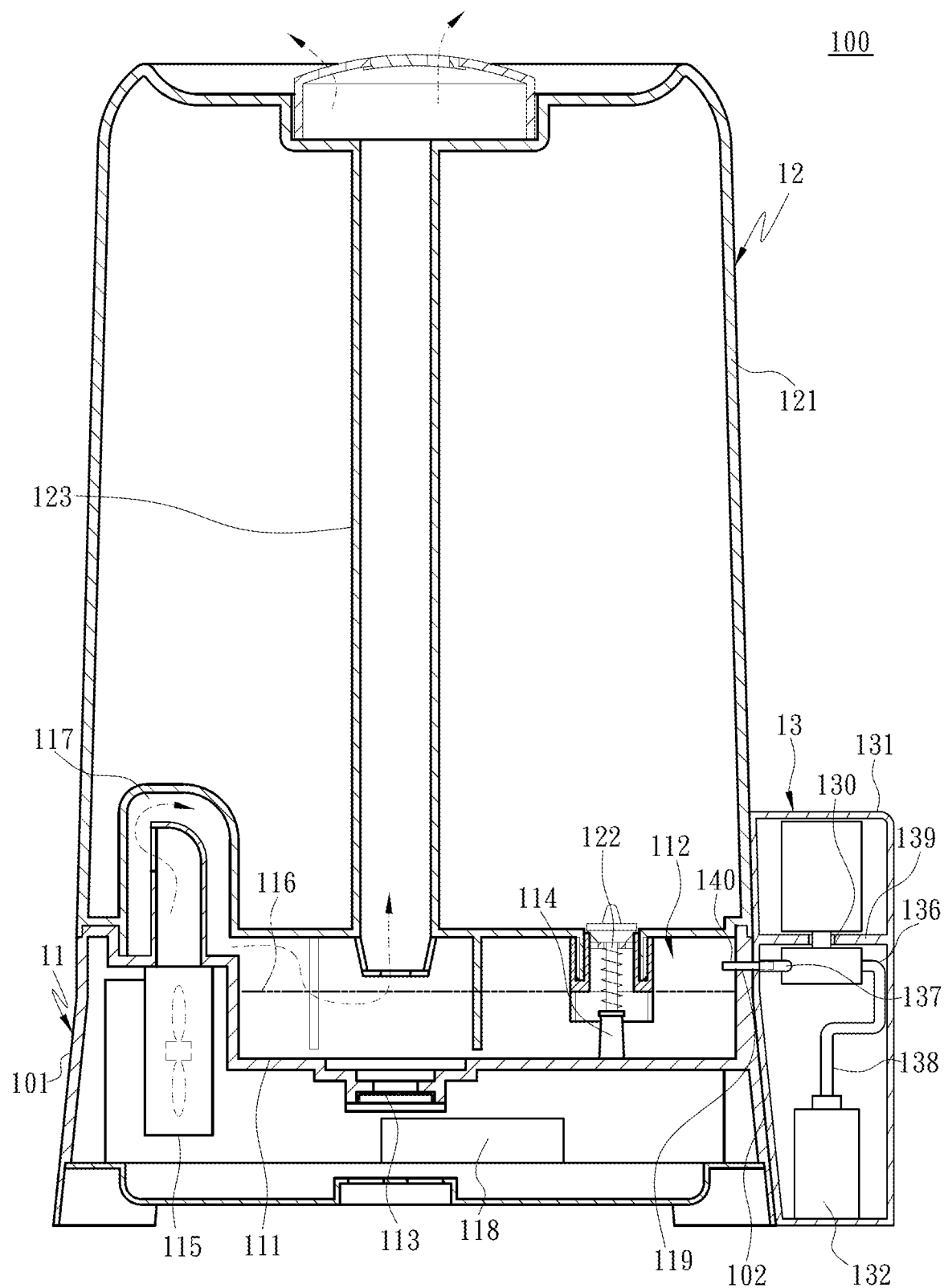
FIG. 3 is a structural cross-section view of one embodiment of the present invention.
Figure 4:
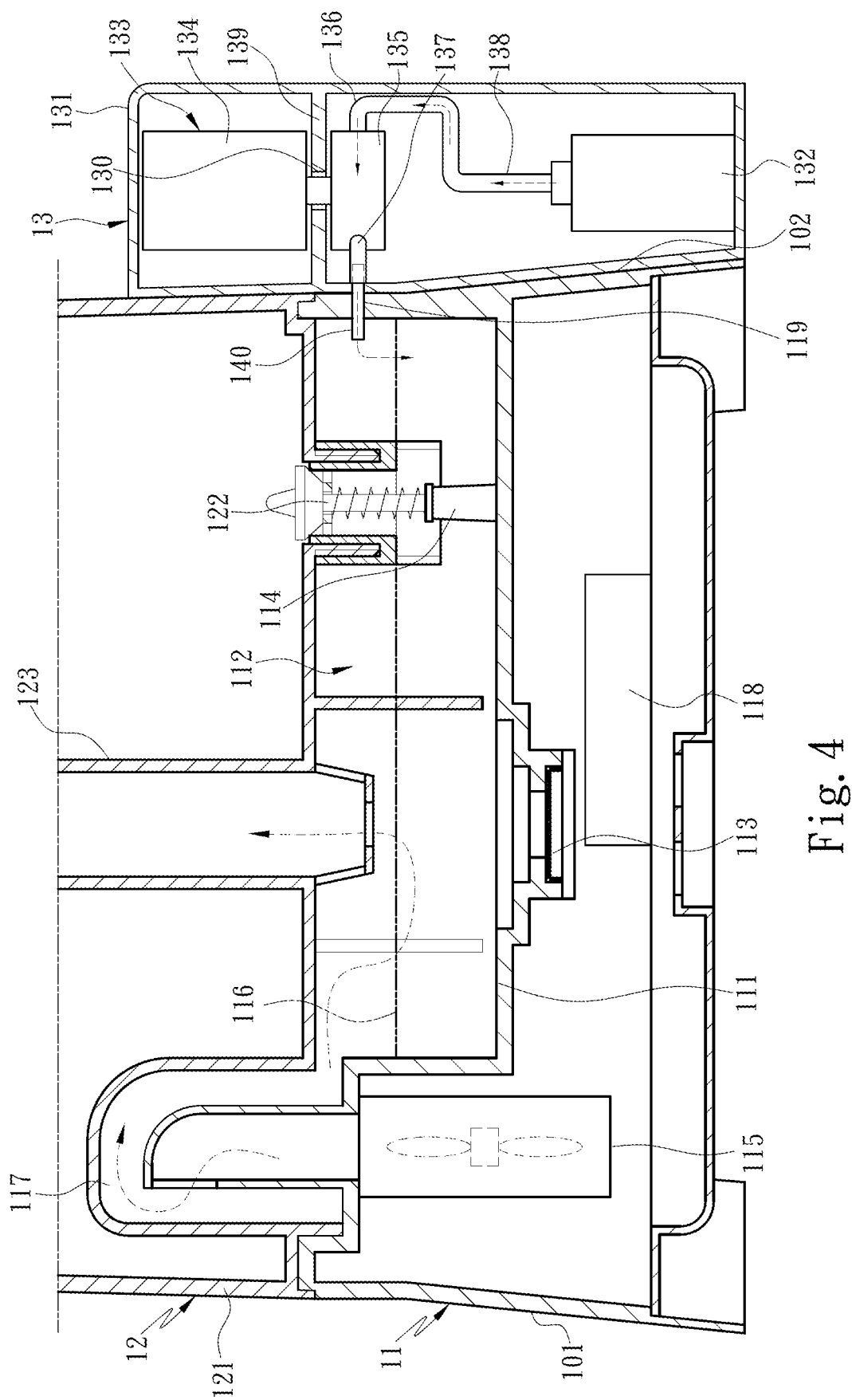
FIG. 4 is a locally structural cross-section view of one embodiment of the present invention.
Figure 5:
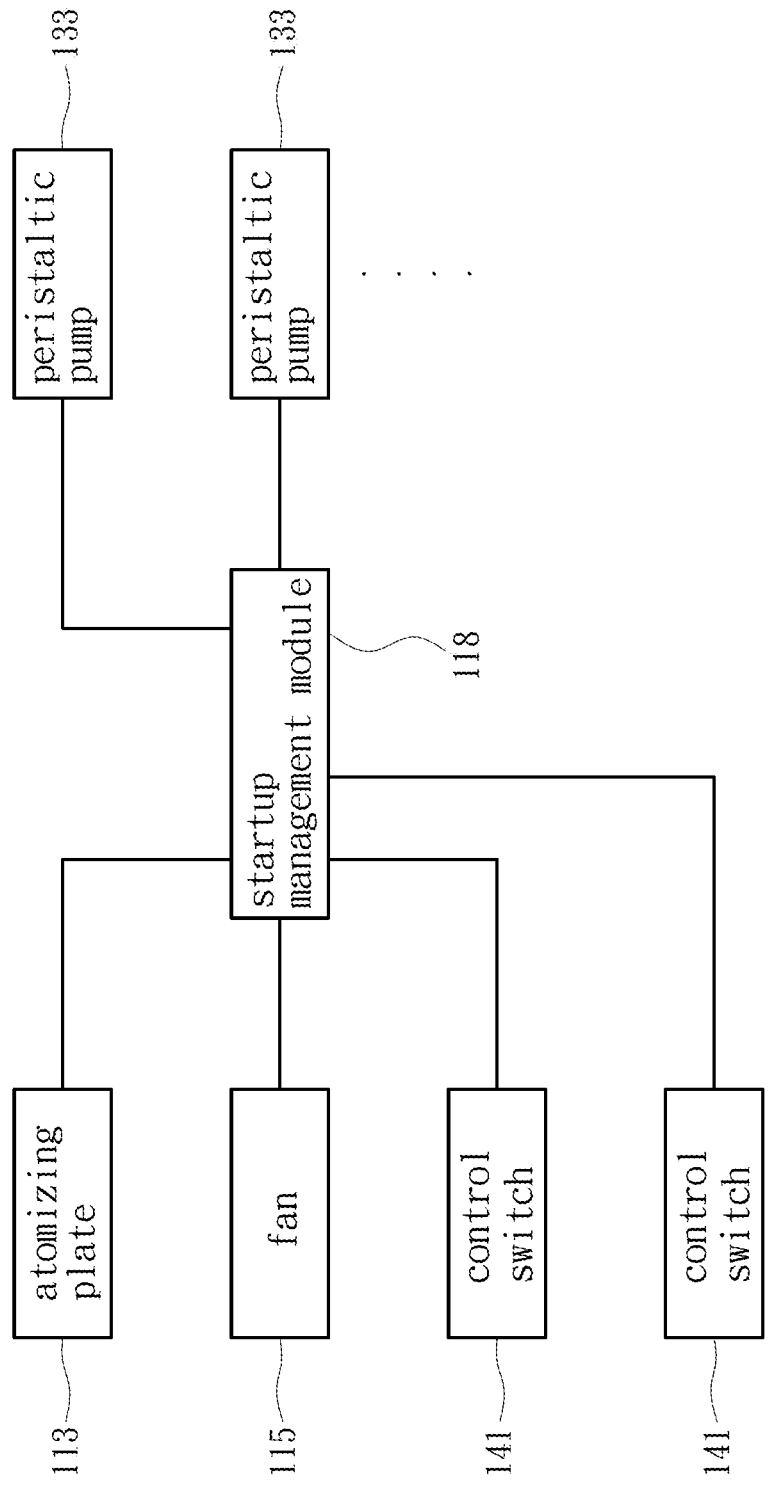
FIG. 5 is a component diagram of one embodiment of the present invention.

The detailed description and technical contents of the present invention are described below with reference to the drawings.

Referring to FIG. 1, FIG. 2, FIG. 3, FIG. 4, and FIG. 5, the present invention provides a humidifier 100 with regular addition of fixed quantity of essential oil, the humidifier 100 being capable of being provided in a larger indoor space, such as a hotel lobby, department store or larger house. The humidifier 100 includes a main body 11 and a water storage bucket 12 mounted to the main body 11. The main body 11 is provided with a temporary liquid storage basin 111, an atomizing space 112 defined by the temporary liquid storage basin 111, an atomizing plate 113 located within the temporary liquid storage basin 111, a projecting stud 114 located within the temporary liquid storage basin 111, a fan 115 generating air stream within the atomizing space 112 after being started. More specifically, the water storage bucket 12 is mounted to the main body 11 at one side where the temporary liquid storage basin 111 is provided, as well as the water storage bucket 12 is capable of supplying the temporary liquid storage basin 111 with water and then allowing a little water being presented in the temporary liquid storage basin 111. Further, the pattern of the temporary liquid storage basin 111 is designed in according with the practical requirement without limitation herein. A high water level line 116 is defined on the temporary liquid storage basin 111, the high water level line 116 indicating a highest water level where pressure in the temporary liquid storage basin 111 and that in the bucket of the water storage bucket 12 are balanced when water is supplied to the temporary liquid storage basin 111 by the water storage bucket 12. Next, the atomizing plate 113 and the projecting stud 114 are provided at the bottom edge of the temporary liquid storage basin 111, respectively, and both of them are provided so as to face one end, which is open, of the temporary liquid storage basin 111. In addition, the main body 11 may be provided with an air stream passage 117 corresponding to the fan 115. The air stream passage 117 is provided at one end thereof on the air-exhaust side of the fan 115, while communicated at the other end thereof to the atomizing space 112. The air stream passage 117 is allowed to guide air stream into the atomizing space 112 when the fan 115 is started. Furthermore, the main body 11 is provided with a startup management module 118 connected to the fan 115 and the atomizing plate 113. The startup management module 118 mainly includes startup control and power supply.

In addition, the water storage bucket 12 is provided with a bucket body 121, a water supply switch 122 provided on the bucket body 121 and pushed by the projecting stud 114 so as to permit water stored in the water storage bucket 12 to flow into the temporary liquid storage basin 111, as well as an air guiding passage 123 defined and formed by the bucket body 121 while communicated to the atomizing space 112 without being used for water storage. Further, the bucket body 121 is configured to store at least one liter of water. The bucket body 121 may be generally annular with hollow center formed as the air guiding passage 123. Moreover, the water supply switch 122 is provided with a first state blocking water supply when the projecting stud 114 is not pushed, and a second state permitting water supply when the projecting stud 114 is pushed.

Furthermore, an essential oil delivering passage 119, corresponding to the temporary liquid storage basin 111, being located higher than the atomizing space 112 and being communicated to the atomizing space 112, is provided on the main body 11 in the present invention. The humidifier 100 is further provided with an essential oil supplier 13 mounted to the main body 11. The essential oil supplier 13 includes a casing 131, at least one essential oil bottle 132 located within the casing 131 and stored with an essential oil, at least one peristaltic pump 133 corresponding to each essential oil bottle 132 and being connected to the startup management module 118. The peristaltic pump 133 is provided with a pump body 134, a peristaltic pump head 135 connected to the pump body 134, and a liquid delivering hose 136 connected to the peristaltic pump head 135. The liquid delivering hose 136 is provided with a liquid supplying end 137 connected to the essential oil delivering passage 119, and a liquid drawing end 138 connected to the essential oil bottle 132. Further, the casing 131 is provided therein with a supporting panel 139. The supporting panel 139 is openly provided with at least one mounting hole 130. The pump body 134 and the peristaltic pump head 135 of the peristaltic pump 133 are located on two sides of the supporting panel 139, respectively. The pump body 134 is connected to the peristaltic pump head 135 through the mounting hole 130.

Referring to FIG. 4 again, when the present invention is put into practice, water stored in the water storage bucket 12 is flowed to the temporary liquid storage basin 111 via the water supply switch 122. When electric power supplied by the startup management module 118 is received by the atomizing plate 113, water stored in the temporary liquid storage basin 111 is transformed into mist by the atomizing plate 113, and meanwhile electric power supplied by the startup management module 118 is also received by the fan 115 to start this fan. Wind generated by the fan 115 is allowed for impelling mist toward the air guiding passage 123, and then mist is discharged through the air guiding passage 123 to humidify the neighborhood. In addition, when the addition of essential oil is desired in the present invention, it is unnecessary to dismount the water storage bucket 12. The peristaltic pump 133 is allowed for rotating the peristaltic pump head 135 to act on the liquid delivering hose 136 when electric power supplied by the startup management module 118 is received by this peristaltic pump. The essential oil within the essential oil bottle 132 is drawn through the liquid drawing end 138, and then guided into the essential oil delivering passage 119 through the liquid supplying end 137 by the liquid delivering hose 136. Afterwards, the essential oil is introduced into the temporary liquid storage basin 111 through the essential oil delivering passage 119. The essential oil will participate in atomization reaction, such that fragrance is added in mist. Additionally, the essential oil is supplied when the peristaltic pump 133 is started by the startup management module 118, and not supplied at one time in the present invention. Even if the peristaltic pump 133 is started over a long period of time, a fixed quantity of essential oil is supplied regularly by means of the peristaltic pump 133. As such, extremely quick volatilization of the essential oil and the resulted incapability of remaining fragrance in mist for a long time, due to the conventional one-off addition of the essential oil, may be avoided.

Figure 6:
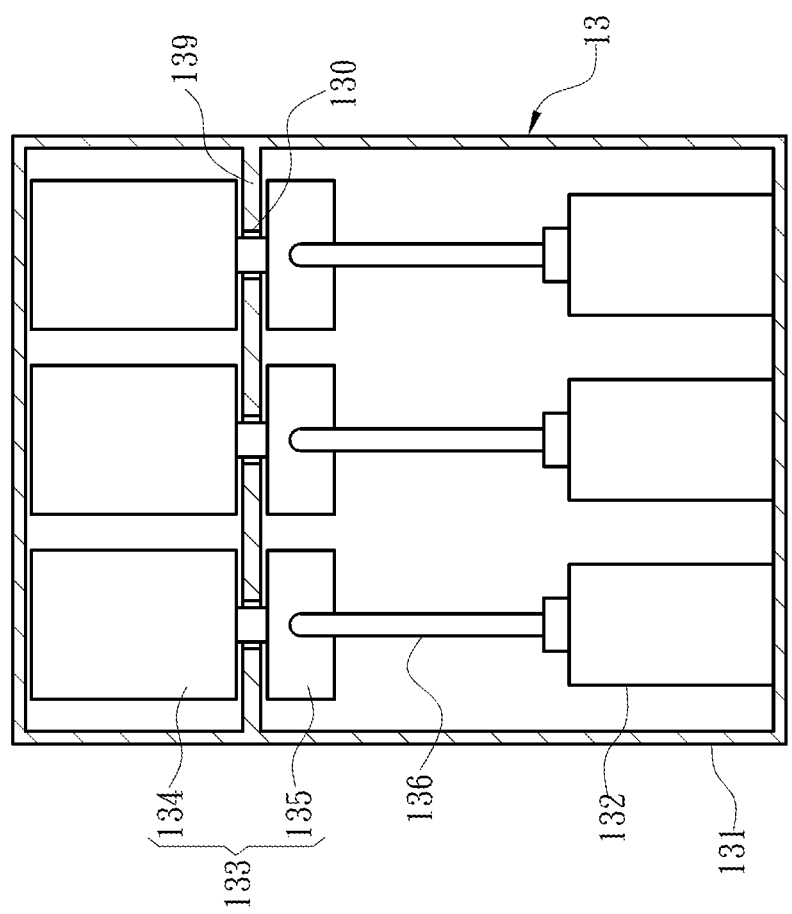
FIG. 6 is a structural view of an essential oil supplier of one embodiment of the present invention.

Besides, referring to FIG. 6 together, the essential oil supplier 13 of the present invention may be provided with a plurality of peristaltic pumps 133 and a plurality of essential oil bottles 132. The types of the essential oil stored within the essential oil bottles 132 may be different from each other. For instance, the lavender essential oil is stored in one of the essential oil bottles 132, while the tangerine essential oil is stored in another one of the essential oil bottles 132. Furthermore, the startup management module 118 may be provided for setting the startup time of each peristaltic pump 133, such that fragrance in mist may be varied on the basis of the time. Additionally, in this embodiment, the fragrance may be no longer one single odor, instead of the startup management module 118 may be configured on the basis of the compound to be implemented desirably, such that the corresponding peristaltic pumps 133 are started by the startup management module 118 on the basis of the compound.

Referring to FIG. 4 again, in one embodiment, the essential oil supplier 13 is provided with a tube 140 located at the end of the liquid delivering hose 136 to be connected to the essential oil delivering passage 119. The tube 140 may be made of metal or plastic, and the bore size of the tube 140 at one end thereof may be configured on the basis of the bore size of the liquid delivering hose 136.

Figure 7:
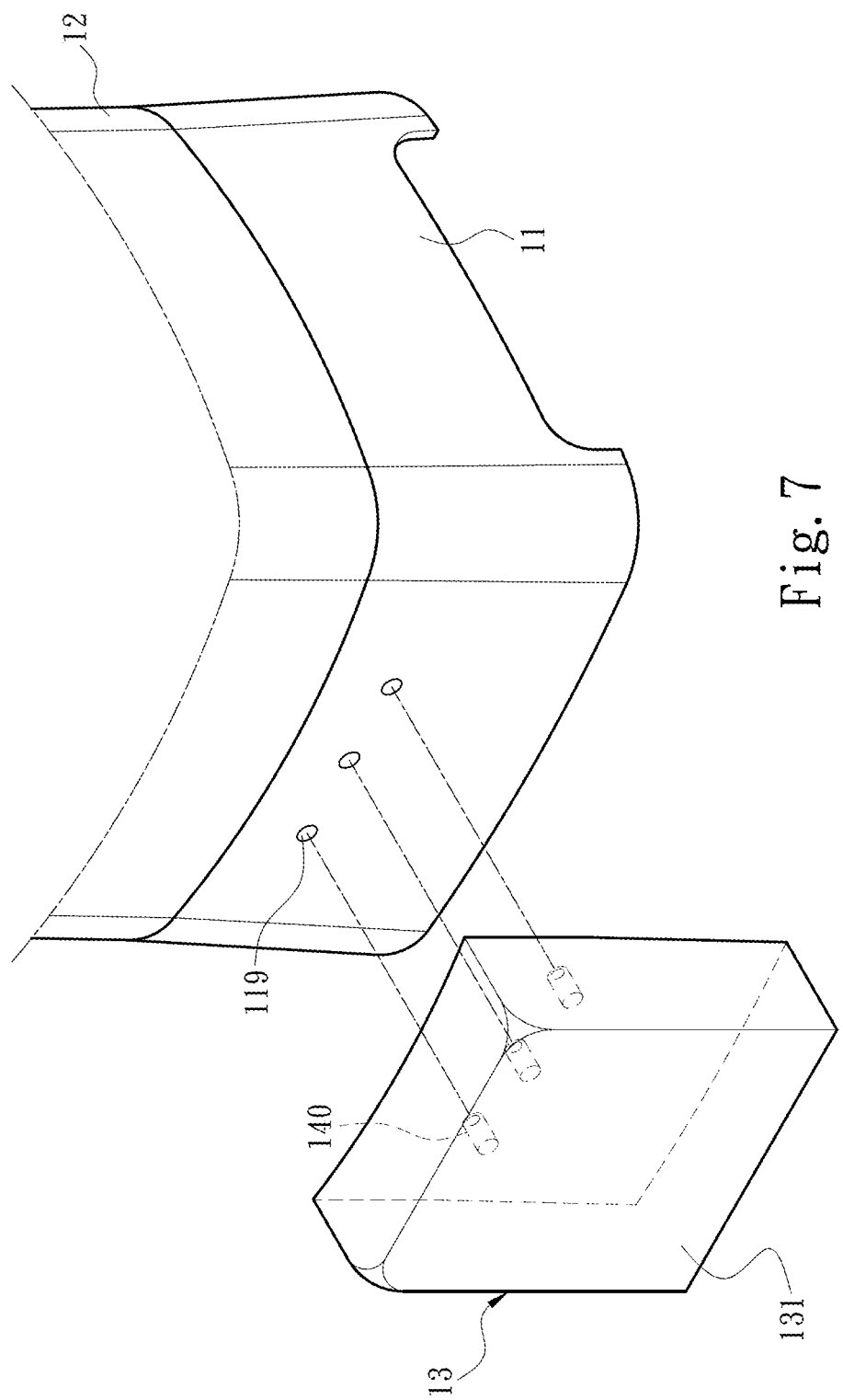
FIG. 7 is a structural exploded view of one embodiment of the present invention.
Figure 8:
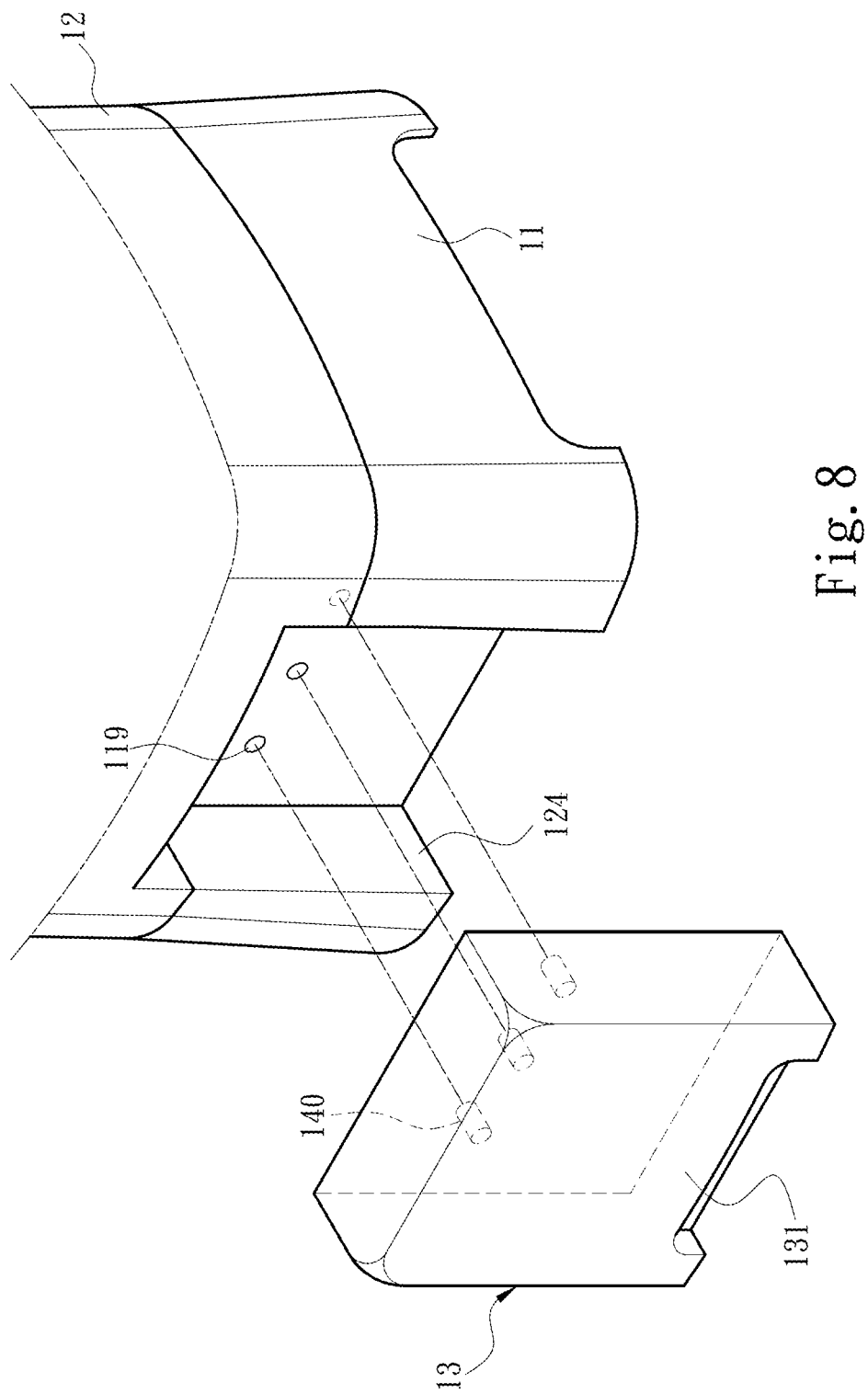
FIG. 8 is a structural disassembled view of another embodiment of the present invention.

Referring to FIG. 7, the essential oil supplier 13 may be dismounted from the main body 11, that is to say, the essential oil supplier 13 may be selectively mounted to the main body 11. When the essential oil supplier 13 is not mounted to the main body 11, humidification of mist is still provided by the humidifier 100. Meanwhile, although water flowed into the temporary liquid storage basin 111 may not be flowed through the essential oil delivering passage 119, one end of the essential oil delivering passage 119 may be closed by means of a plug (not shown in the figure) or a cover (not shown in the figure). Furthermore, referring to FIG. 8, the bucket body 121 in one embodiment includes an accommodating recess 124 provided for the essential oil supplier 13 to be selectively located therein without being prominently projected on the exterior of the water storage bucket 12. Thereby, the essential oil supplier 13 is located within the accommodating recess 124 without being prominently projected on the exterior of the water storage bucket 12, such that the water storage bucket 12 is more aesthetically pleasing in the whole appearance.

Referring to FIG. 1, FIG. 2, FIG. 3, FIG. 4, and FIG. 5 again, the main body 11 includes a plurality of control switches 141 connected to the startup management module 118 and appeared at the outside of the main body 11. Each of the plurality of control switches 141 may be controlled so as to output a control signal to the startup management module 118. Each control signal outputted from each of the plurality of control switches 141 may be defined as an individual control message, such that the startup management module 118 is allowed for performing, after receiving each control signal, a corresponding operation in accordance with the configured control procedure. For instance, one of the plurality of control switches 141 may be used for starting atomization, while another one of the plurality of control switches 141 may be used for supplying essential oil. Additionally, the number of the plurality of control switches 141, configured for supplying essential oil, is not only single one, and may be adjusted on the basis of the essential oil bottles 132. For instance, if three essential oil bottles 132 are allowed to be provided in the essential oil supplier 13, the number of the plurality of control switches 141 is three. In one embodiment, referring to FIG. 1, FIG. 2, FIG. 3 and FIG. 4 again, the main body 11 is provided with a front side 101 having the plurality of control switches 141, and a rear side 102 having the essential oil supplier 13.

Please refer to FIG. 9, FIG. 10, FIG. 11, FIG. 12, FIG. 13, FIG. 14, FIG. 15, FIG. 16, and FIG. 17. In addition to the humidifier 100 described above, the present invention also provides another embodiment. The basic structure of the humidifier 100 in this embodiment is the same as that of the humidifier 100 in the previous embodiment. The difference between the two humidifiers 100 is that the essential oil bottle 132 is installed in an essential oil bottle accommodation space 144 inside the main body 11 in this embodiment, that is, the essential oil bottle 132 is not exposed outside the main body 11 after the installation is complete.

Figure 9:
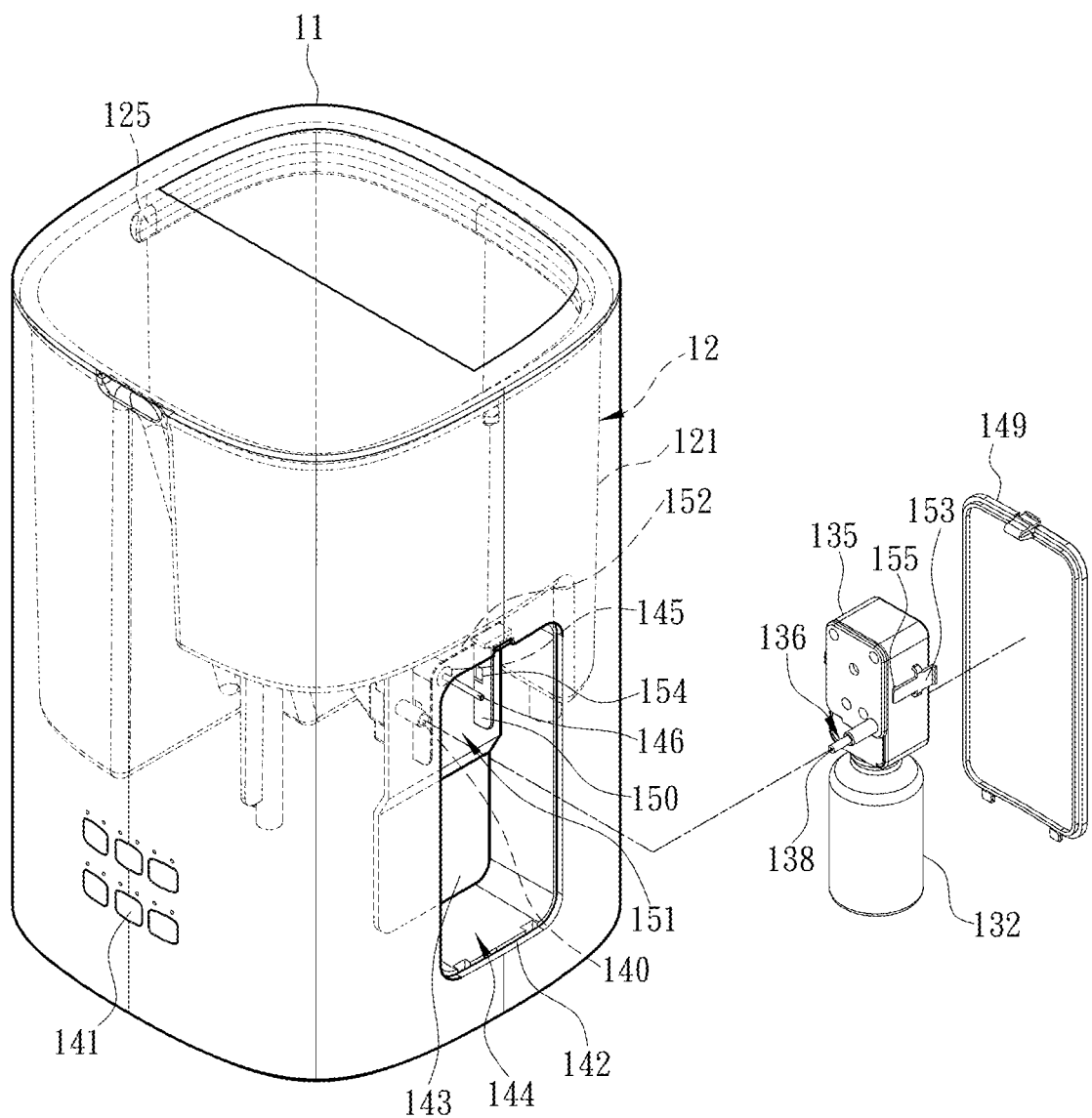
FIG. 9 is a first perspective structural exploded view of another embodiment of the present invention.
Figure 10:
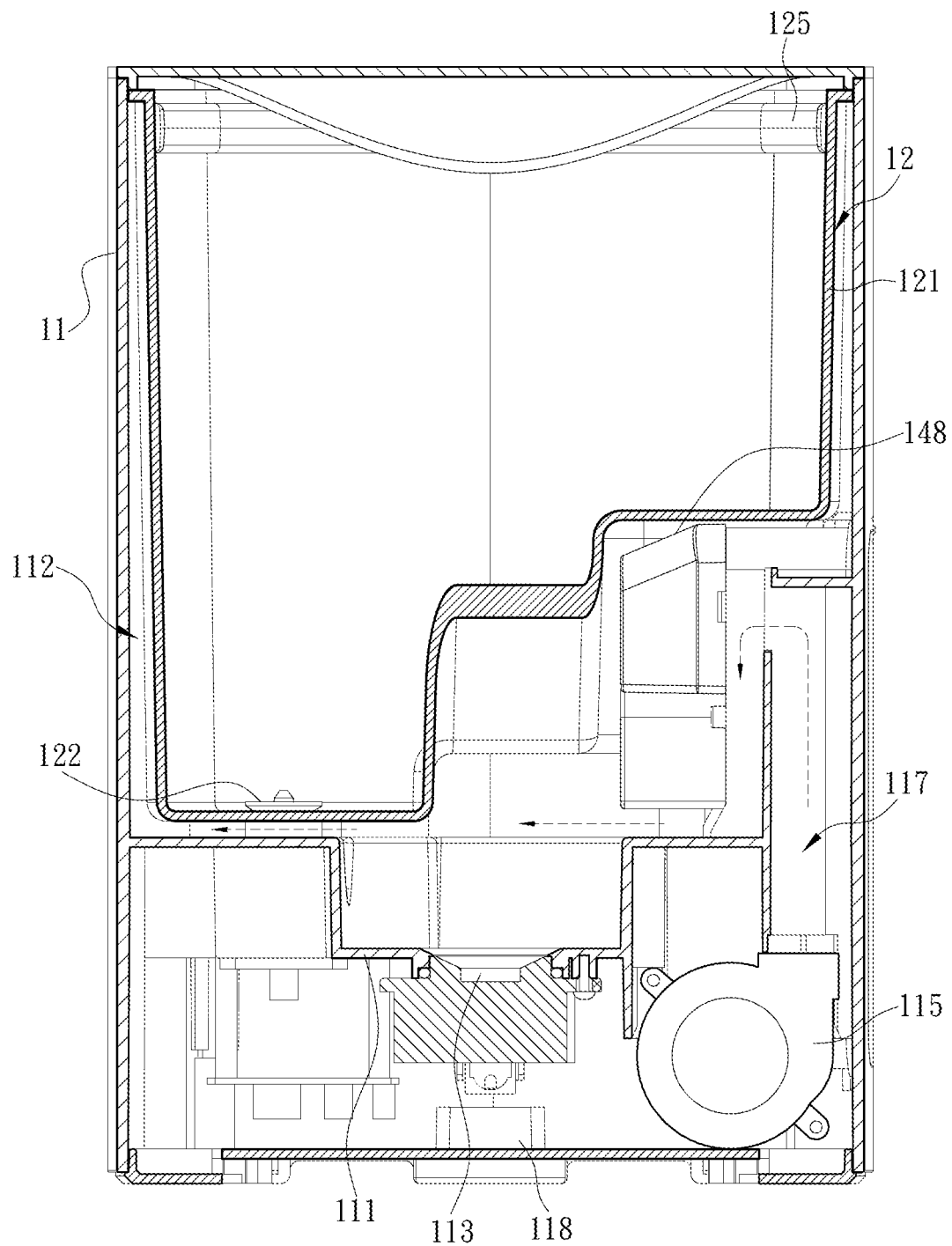
FIG. 10 is a structural cross-section view of another embodiment of the present invention.
Figure 13:
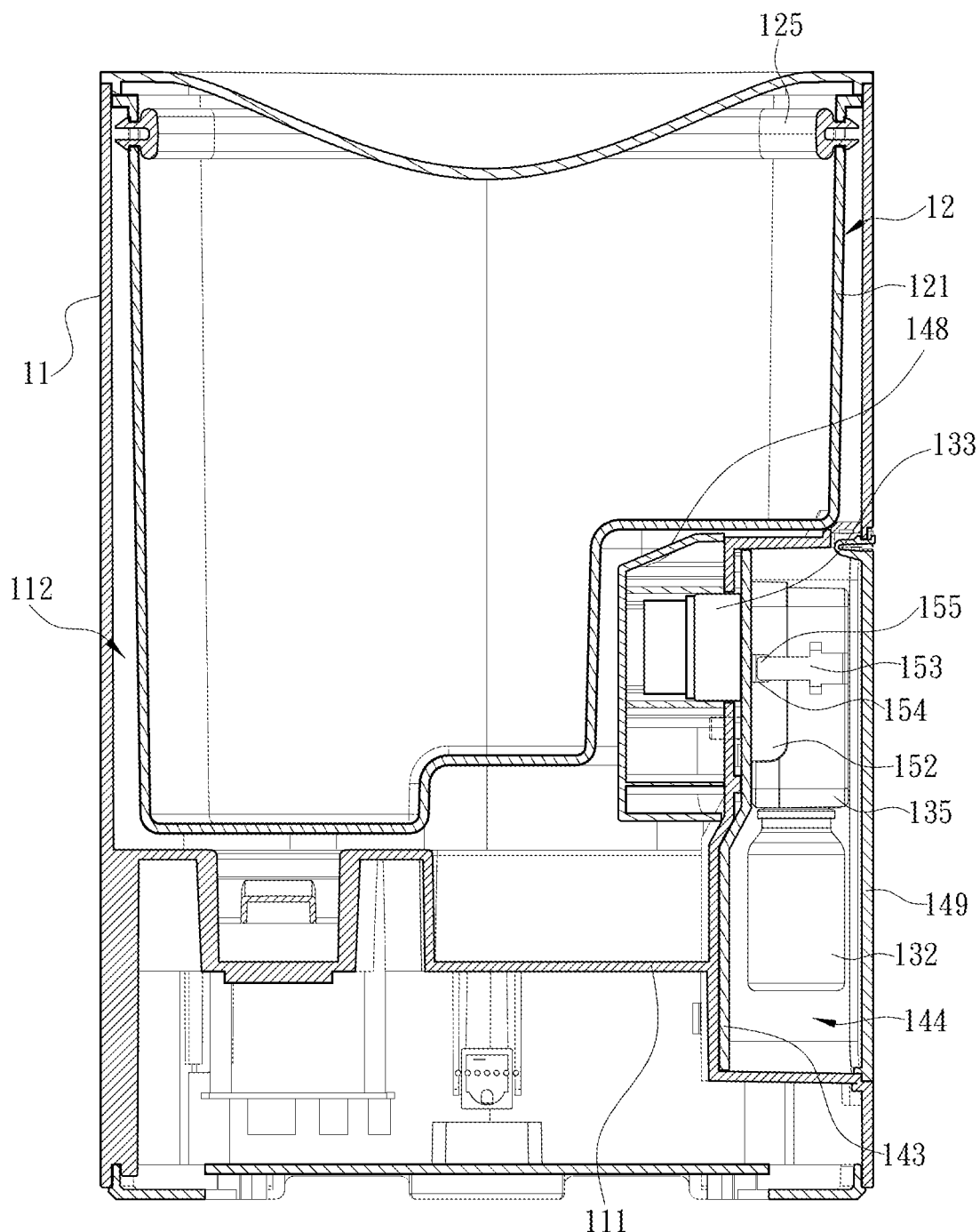
FIG. 13 is a cross-sectional view of A-A line of FIG. 12 of another embodiment of the present invention.
Figure 14:
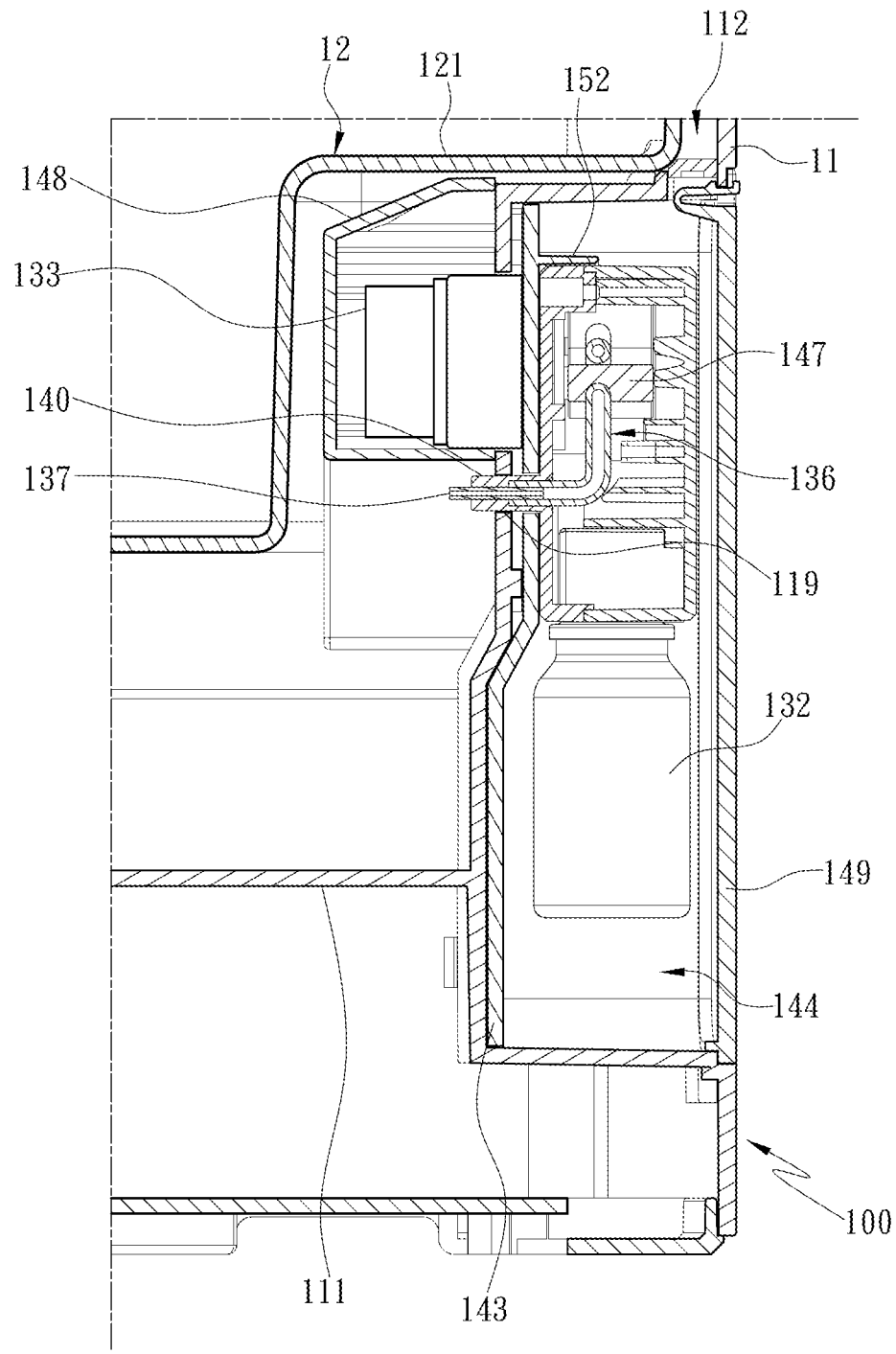
FIG. 14 is a partially enlarged view of FIG. 13 of another embodiment of the present invention.
Figure 15:
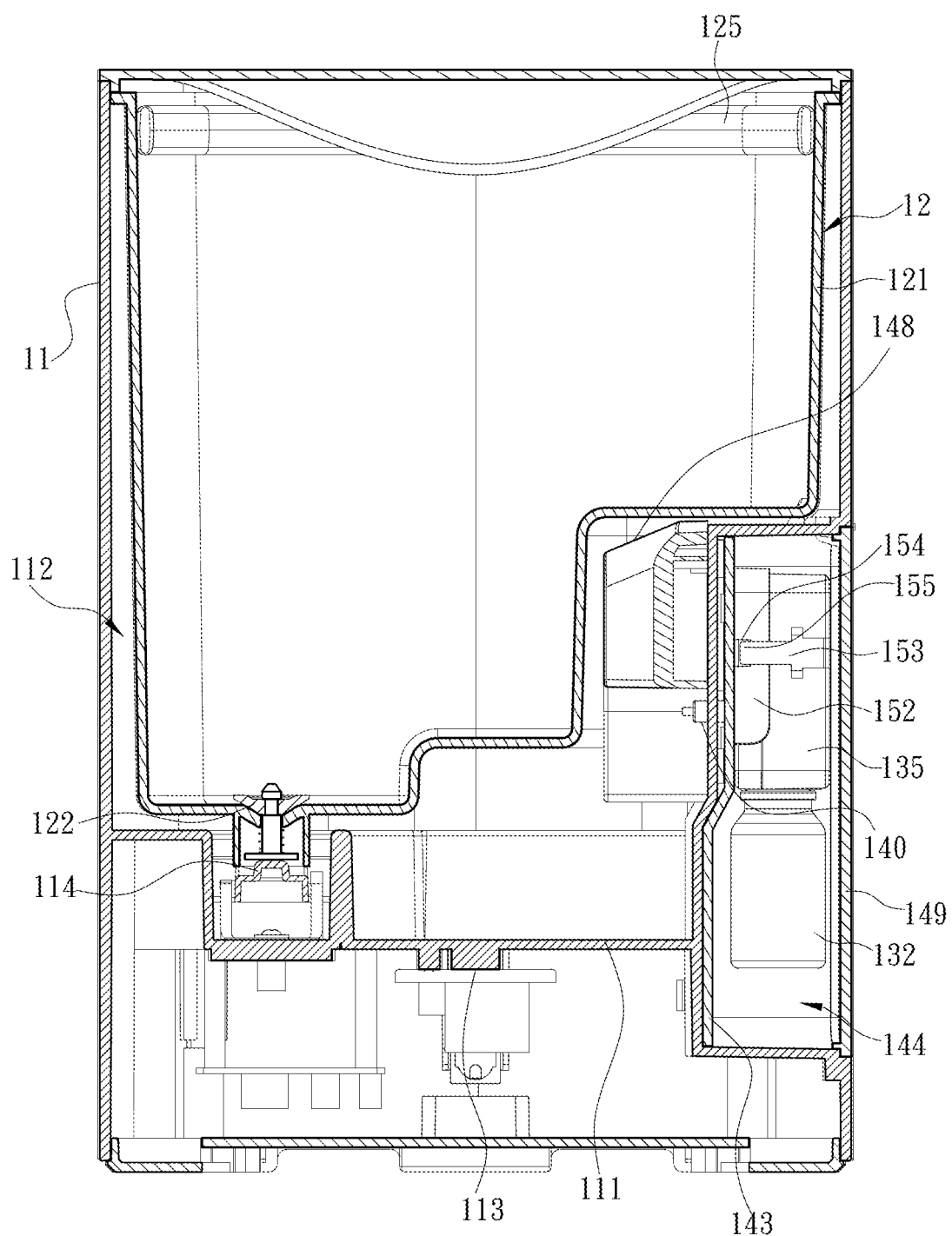
FIG. 15 is a cross-sectional view of B-B line of FIG. 12 of another embodiment of the present invention.

Please refer to FIG. 9, FIG. 10, and FIG. 13. Specifically, in addition to the peristaltic pump 133, the main body 11 further includes at least one opening 142 located on one side of the main body 11, and an inner casing 143 disposed inside the main body 11 and corresponding to the opening 142. A side of the inner casing 143 that does not face the opening 142 is provided for the peristaltic pump 133 to be disposed thereon. Further, the inner casing 143 defines the essential oil bottle accommodation space 144 communicating with the opening 142. In addition to the inner casing 143 comprising the tube 140 with one end facing the temporary liquid storage basin 111, a through hole 145 is further formed on the inner casing 143. When the peristaltic pump 133 is assembled on the inner casing 143, the through hole 145 is provided for a transmission shaft 146 of the peristaltic pump 133 to pass through.

Figure 11:
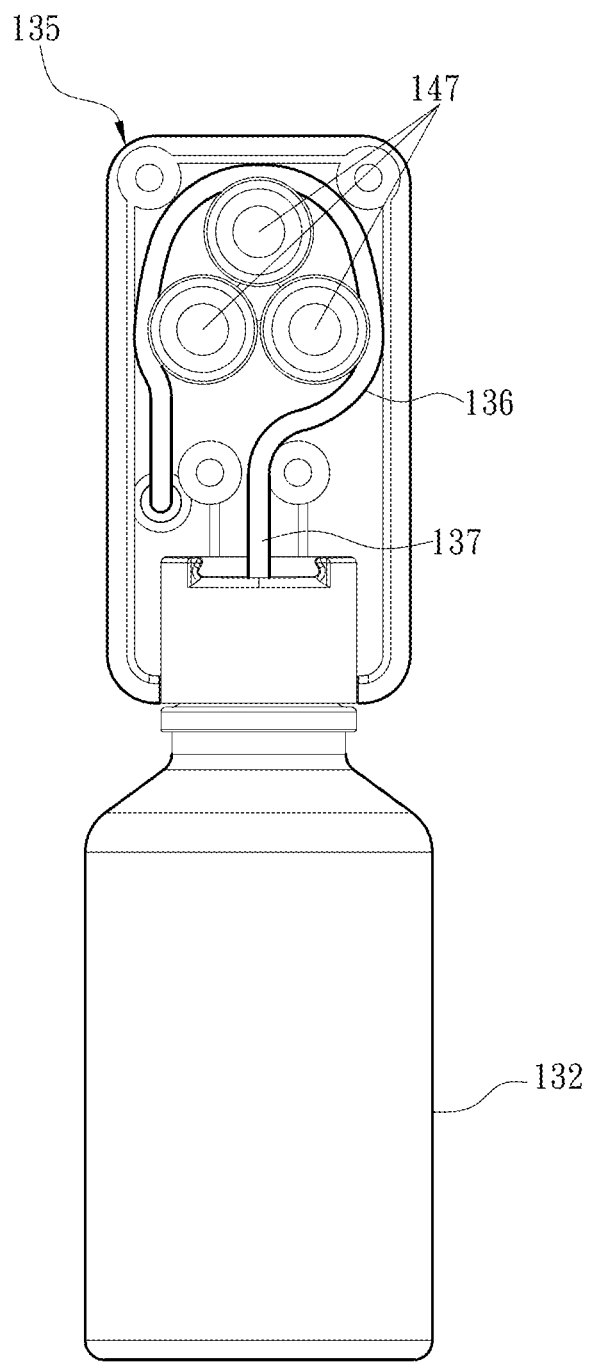
FIG. 11 is a structural view of the essential oil supplier of another embodiment of the present invention.
Figure 12:
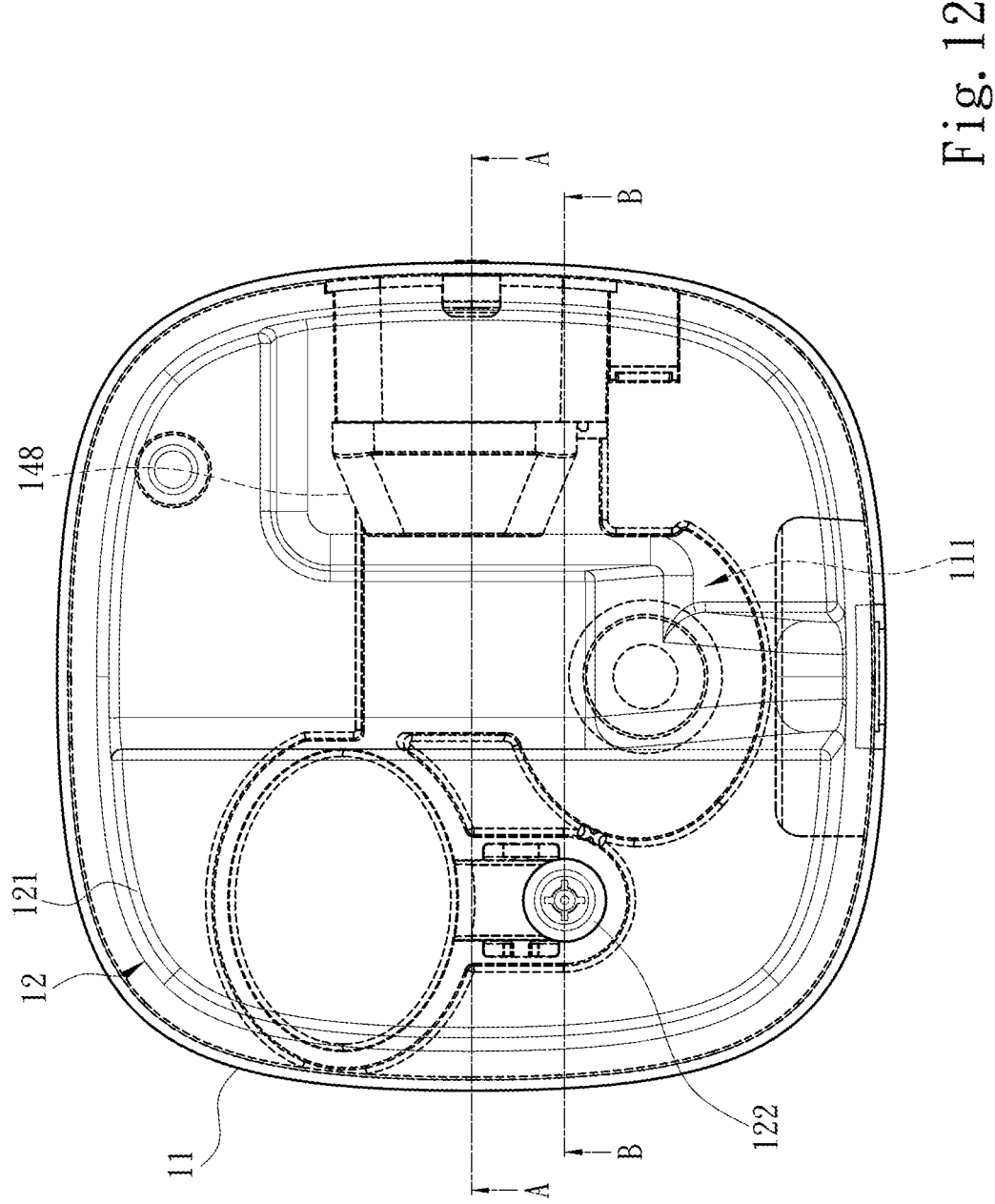
FIG. 12 is a top view of another embodiment of the present invention.

Furthermore, please refer to FIG. 9, FIG. 10, and FIG. 11. In this embodiment, the peristaltic pump head 135 is assembled with the transmission shaft 146 and driven by the transmission shaft 146. Specifically, inside the peristaltic pump head 135 is provided with a plurality of rollers 147 and the liquid delivering hose 136. The plurality of rollers 147 is connected to the transmission shaft 146 and forms a transmission relationship with the transmission shaft 146. The plurality of rollers 147 is assembled with the liquid delivering hose 136 at the same time, when the plurality of rollers 147 is driven by the transmission shaft 146 to rotate, the liquid delivering hose 136 is driven to deliver liquid simultaneously. Also, in this embodiment, the peristaltic pump head 135 and the essential oil bottle 132 form an integrated structure, and the integrated structure is selectively installed into the essential oil bottle accommodation space 144 through the opening 142 or taken out from the essential oil bottle accommodation space 144.

Then, please refer to FIG. 9, FIG. 10, FIG. 11, FIG. 12, FIG. 13, and FIG. 14. When the present invention is implemented, water stored in the water storage bucket 12 flows to the temporary liquid storage basin 111 via the water supply switch 122, and the water stored in the temporary liquid storage basin 111 is transformed into mist by the atomizing plate 113. At the same time, the fan 115 is actuated by electric power supplied by the startup management module 118. Air current generated by the fan 115 causes the mist to flow toward the air stream passage 117, and then the mist is discharged through the atomizing space 112 to humidify the adjacent area. On the other hand, the peristaltic pump 133 receives the electric power supplied by the startup management module 118, so that the transmission shaft 146 starts to rotate and drives the plurality of rollers 147 to rotate. The plurality of rollers 147 drives the liquid delivering hose 136 while rotating, so that the liquid delivering hose 136 draws the essential oil in the essential oil bottle 132 through the liquid drawing end 138, and then guided into the essential oil delivering passage 119 through the liquid supplying end 137. Afterwards, the essential oil is introduced into the temporary liquid storage basin 111 through the essential oil delivering passage 119, and the essential oil participates in atomization reaction, such that fragrance is added in the mist.

Accordingly, in this embodiment, the peristaltic pump head 135 is not provided with the peristaltic pump 133, so that when the humidifier 100 is required to be replaced with the different essential oil bottle 132, a user does not need to replace the peristaltic pump 133 together, and consumers are able to drastically reduce costs. Meanwhile, in this embodiment, the liquid delivering hose 136 is disposed in the peristaltic pump head 135, so that the user can dismount the liquid delivering hose 136 when replacing the different peristaltic pump head 135 and the essential oil bottle 132. Thus, the scent of fragrance used in the humidifier 100 is unchanged since the essential oil with different fragrances is prevented from mixing in the liquid delivering hose 136.

Please refer to FIG. 9 and FIG. 13. In one embodiment, to separate the peristaltic pump 133 from the atomizing space 112, the main body 11 comprises a protective cover 148 disposed on a side of the inner casing 143 that does not face the opening 142, and the protective cover 148 is assembled with the inner casing 143 to cover the peristaltic pump 133, thereby avoiding problems such as electric short circuit caused by the peristaltic pump 133 contacting with the mist in the atomizing space 112. On the other hand, please refer to FIG. 9 and FIG. 14, the water storage bucket 12 comprises a handle 125 for carrying. In addition, the main body 11 comprises a lid 149 provided corresponding to the opening 142, and the lid 149 is assembled on the opening 142 to seal the essential oil bottle accommodation space 144. In this way, the peristaltic pump head 135 and the essential oil bottle 132 are assembled with each other in the essential oil bottle accommodation space 144, and the appearance of the humidifier 100 is more aesthetic.

Figure 16:
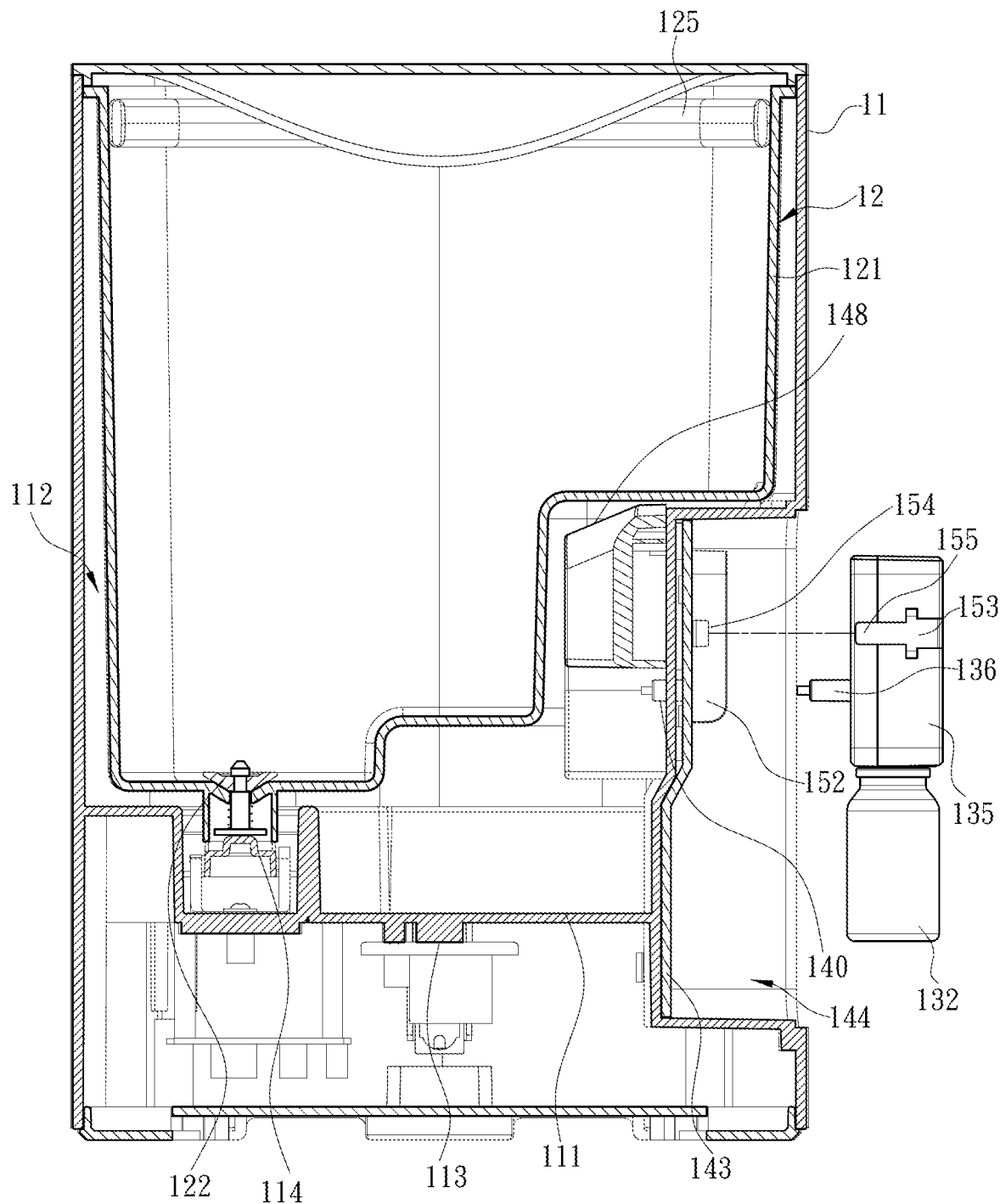
FIG. 16 is a cross-sectional view of a part of components of another embodiment of the present invention.
Figure 17:
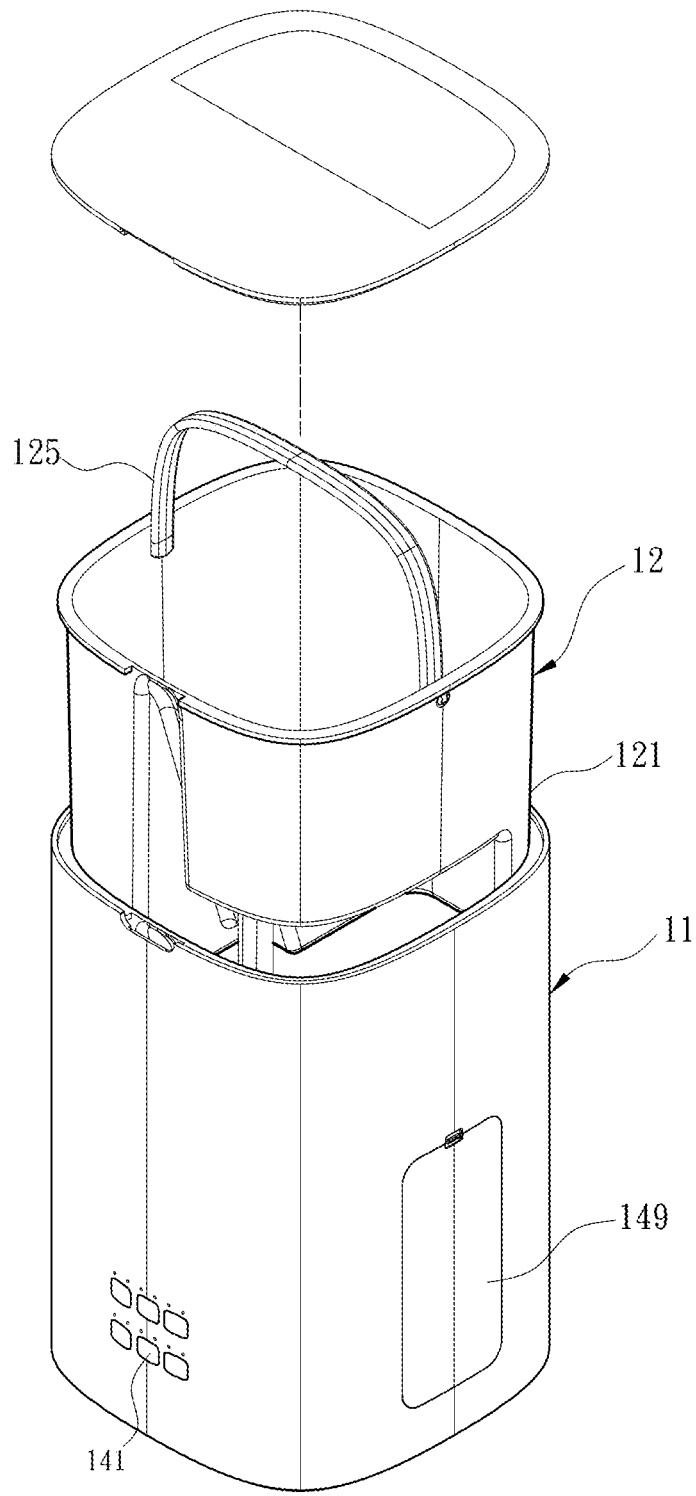
FIG. 17 is a second perspective structural exploded view of another embodiment of the present invention.

Please refer to FIG. 9 and FIG. 16. To stably dispose the peristaltic pump head 135 in the essential oil bottle accommodation space 144, the inner casing 143 is provided with two limit plates 150 spaced apart from each other, and a pump head installation zone 151 is defined between the two limit plates 150. A width of the pump head installation zone 151 is equal to a width of the peristaltic pump head 135, so that the peristaltic pump head 135 is placed into the pump head installation zone 151 and assembled with the two limit plates 150. Further, the inner casing 143 comprises a connecting plate 152 connected to the two limit plates 150. The pump head installation zone 151 is defined by the connecting plate 152 together with the two limit plates 150. The connecting plate 152 is connected to one side of each of the two limit plates 150 facing the water storage bucket 12. Considering the connecting plate 152 and the two limit plates 150 are respectively assembled with the peristaltic pump head 135, the connecting plate 152 and the two limit plates 150 partly cover the peristaltic pump head 135, thereby easily for removing or installing the peristaltic pump head 135 from one side of the two limit plates 150 not connected to the connecting plate 152.

Further, to stably assemble the peristaltic pump head 135 with the two limit plates 150, the peristaltic pump head 135 is provided with a connecting arm 153 on both sides respectively. Each of the two limit plates 150 comprises a positioning structure 154 corresponding to the connecting arm 153, and the positioning structure 154 is assembled with one of the connecting arms 153 to fix the peristaltic pump head 135 on the two limit plates 150. Further, each of the positioning structures 154 is a through hole, and one end of the connecting arm 153 assembled with the positioning structure 154 is provided with a hook 155. In the present invention, through the hook 155 hooked into one of the through holes, the peristaltic pump head 135 is limited on the two limit plates 150.

What is claimed is:

1. A humidifier with regular addition of fixed quantity of essential oil, the humidifier including a main body, and a water storage bucket assembling with the main body, the main body comprising a temporary liquid storage basin, an atomizing space defined by the temporary liquid storage basin, an atomizing plate disposed within the temporary liquid storage basin, a projecting stud disposed within the temporary liquid storage basin, a fan generating air stream within the atomizing space after being started, and a startup management module connected to the fan and the atomizing plate, a high water level line is defined on the temporary liquid storage basin, the water storage bucket comprising a bucket body, a water supply switch provided on the bucket body and pushed by the projecting stud to permit water stored in the water storage bucket to flow into the temporary liquid storage basin, and an air guiding passage defined and formed by the bucket body while communicated to the atomizing space without being used for water storage; and the humidifier characterized in that:

the main body comprises at least one opening located on one side, an inner casing disposed inside the main body and corresponding to the opening, and a peristaltic pump provided on a side of the inner casing not facing the opening, the inner casing defines an essential oil bottle accommodation space communicating with the opening, the inner casing is disposed with a through hole and an tube, wherein the through hole is provided for a transmission shaft of the peristaltic pump to pass through, and one end of the tube faces the temporary liquid storage basin, the humidifier comprises a peristaltic pump head provided in the essential oil bottle accommodation space and driven by the peristaltic pump, in the peristaltic pump head is provided with a plurality of rollers driven by the transmission shaft, and a liquid delivering hose disposed between the plurality of rollers, one end of the liquid delivering hose reaches into an essential oil bottle, and another end is connected to the tube.

2. The humidifier with regular addition of fixed quantity of essential oil as claimed in claim 1, wherein the main body comprises a lid disposed corresponding to the opening to seal the essential oil bottle accommodation space.

3. The humidifier with regular addition of fixed quantity of essential oil as claimed in claim 1, wherein the inner casing comprises two limit plates spaced apart from each other, a pump head installation zone is defined by the two limit plates, and the through hole and one end of the tube are located in the pump head installation zone.

4. The humidifier with regular addition of fixed quantity of essential oil as claimed in claim 3, wherein the inner casing comprises a connecting plate connected to the two limit plates and the pump head installation zone is defined by the connecting plate together with the two limit plates.

5. The humidifier with regular addition of fixed quantity of essential oil as claimed in claim 3, wherein the peristaltic pump head is provided with a connecting arm on both sides respectively, and each of the two limit plates comprises a positioning structure assembled with the connecting arm.

6. The humidifier with regular addition of fixed quantity of essential oil as claimed in claim 5, wherein one end of the connecting arm assembled with the positioning structure is provided with a hook.

7. The humidifier with regular addition of fixed quantity of essential oil as claimed in claim 6, wherein each positioning structure is a through hole providing for one of the hooks to dispose.

8. The humidifier with regular addition of fixed quantity of essential oil as claimed in claim 1, wherein the main body comprises a protective cover disposed on a side of the inner casing that does not face the opening and covering the peristaltic pump.

9. The humidifier with regular addition of fixed quantity of essential oil as claimed in claim 1, wherein the main body includes a plurality of control switches connected to the startup management module and exposed outside the main body.

* * * * *